United States Patent [19]

Rao et al.

[11] 4,233,248
[45] Nov. 11, 1980

[54] PROCESS FOR OXIDATION OF METHANOL TO FORMALDEHYDE WITH NITROUS OXIDE

[75] Inventors: V. N. Mallikarjuna Rao; Stanislaw B. Ziemecki, both of Wilmington, Del.

[73] Assignee: E. I. Du Pont de Nemours and Company, Wilmington, Del.

[21] Appl. No.: 13,122

[22] Filed: Feb. 21, 1979

[51] Int. Cl.$^3$ .................. C07C 47/052; C07C 45/29
[52] U.S. Cl. ............................................. 568/487
[58] Field of Search ............... 260/606, 603 C, 601 B

[56] References Cited

U.S. PATENT DOCUMENTS

| | | | |
|---|---|---|---|
| 2,667,513 | 1/1954 | McKinnis | 260/606 |
| 4,119,673 | 10/1978 | Aicher et al. | 260/606 |

Primary Examiner—Werren B. Lone

[57] ABSTRACT

Formaldehyde is synthesized by continuously passing a gaseous mixture of methanol and nitrous oxide over a metallic silver-containing catalyst bed at a temperature of about 475 to about 675° C.

12 Claims, No Drawings

PROCESS FOR OXIDATION OF METHANOL TO FORMALDEHYDE WITH NITROUS OXIDE

TECHNICAL FIELD

This invention relates to an improved process for the synthesis of formaldehyde by the oxidation of methanol over a silver catalyst at elevated temperatures.

BACKGROUND ART

Formaldehyde is commercially manufactured at the present time by passing methanol vapors in the presence of oxygen (air) over a silver catalyst, for example, over fine silver gauze, or granules, at temperatures in excess of 500° C. or an oxide catalyst such as iron molybdate at lower temperatures. Formaldehyde may also be obtained in small yield by the partial oxidation of hydrocarbons such as ethane, ethylene and natural gas or by the oxidation of dimethylether.

DISCLOSURE OF INVENTION

According to this invention, there is provided a process for the preparation of formaldehyde involving contacting, for a period of time ranging between about 0.001 and about 0.2 second, a gaseous mixture of methanol and nitrous oxide in a methanol to nitrous oxide mole ratio ranging between about 0.5 and about 4.0 with a metallic silver-containing catalyst bed maintained at a temperature of about 475° to about 675° C. The principle advantage of this process is that it results in a higher conversion of methanol and a higher selectivity to formaldehyde than prior art processes utilizing oxygen or air rather than nitrous oxide.

As previously mentioned, formaldehyde is presently prepared by contacting methanol vapors with air or oxygen over a silver catalyst at elevated temperatures. The crux of the present invention lies in utilizing nitrous oxide instead of air or oxygen as the oxygen source with improved yeilds of formaldehyde. At the preferred operating temperatures, nitrous oxide is converted over silver, yielding gaseous nitrogen and atomic oxygen species adsorbed on the catalyst. The use of oxygen in the atomic form is believed to result in higher conversion of methanol and higher selectivity to formaldehyde. The principal advantage of this process lies in combining the quantitative decomposition of nitrous oxide with highly selective conversion of methanol to formaldehyde.

In a preferred mode of operation, the process of the present invention involves the synthesis of formaldehyde by contacting a gaseous mixture of methanol and nitrous oxide with a bed of silver catalyst kept at the desired operating temperature in a continuous flow reactor.

The feed contains a gaseous mixture of methanol and nitrous oxide in which the mole ratio of $CH_3OH/N_2O$ ranges between about 0.5 and about 4.0, with the range of about 1.0 to about 2.5 being preferred. In a preferred embodiment, the gaseous mixture of methanol and nitrous oxide is diluted with an inert gas. The term "inert gas" is intended to mean gases which are not reactive with methanol, formaldehyde, nitrous oxide or the silver catalyst under the reaction conditions, and includes helium, neon, argon and nitrogen, as well as mixtures thereof.

The catalyst employed must contain metallic silver. It can be used as pure metal, for example, silver gauze or granules, or as silver supported on an inert material such as $\alpha$-alumina, or as an alloy of silver with other metals, such as gold and copper. Pure silver catalysts, unsupported or supported on $\alpha$-alumina, are preferred over the alloy catalysts. Supported catalysts should contain a minimum of at least about 3% by weight of silver. Alloys should contain at least 2.5 mole percent of silver.

The catalyst bed can be operated at temperatures between about 475° and about 675° C. with the preferred operating temperature ranging between about 550° and about 650° C. The contact time of the gaseous reactants with the catalyst should be short enough to avoid further conversion of formaldehyde and recombination of the atomic oxygen species, but long enough to maximize methanol conversion. Contact times ranging between about 0.001 and about 0.2 second are satisfactory, with contact times of about 0.001 to about 0.1 second being preferred. Experience has shown that the shorter the contact time, the better the selectivity achieved. In commercial operations contact times of about 0.001 to about 0.005 are most preferred. These short contact times, however, are difficult to achieve under laboratory conditions.

BEST MOLD

The best mode contemplated for carrying out the invention involves contacting, for a period of time ranging between 0.03 and 0.1 second, a gaseous mixture of methanol and nitrous oxide diluted with an inert gas, in which the mole ratio of methanol to nitrous oxide is within the range of 1.0 to 2.5, with a pure metallic silver catalyst maintained at a temperature of 550° to 650° C.

The following examples more fully illustrate the invention.

EXAMPLE 1

A. A mixture of $CH_3OH$ and $N_2O$ in helium, in which the mole ratio of $CH_3OH$ to $N_2O$ was 2, was passed over 0.5 g. of silver granules having an average particle diameter of $2 \times 1$ mm. at 599° C. with a contact time of 0.1 second. After 59 minutes on stream, an 86% conversion of methanol and a 63% yield of formaldehyde was achieved.

B. The above process was repeated with the exception that the concentration of $N_2O$ in the feed was increased by a factor of 2 so that the mole ratio of $CH_3OH$ to $N_2O$ was 1. The result was a 92% methanol conversion to give a 56% yield of formaldehyde.

C. For comparison, part A above was repeated with the exception that molecular oxygen was substituted for $N_2O$. In order to equate the oxidizing power of the oxygen to that of nitrous oxide, the mole ratio of methanol to oxygen was 4.0. After 71 minutes at 595° C., the conversion of methanol was 50% with a 54% yield of formaldehyde.

EXAMPLE 2

A mixture of $CH_3OH$ and $N_2O$ in helium, in which the mole ratio of $CH_3OH$ to $N_2O$ was 1.57, was oxidized over the metallic silver catalyst described in Example 1 at a contact time of 0.08 second. When the temperature was 550° C. 85% methanol conversion and 66% formaldehyde yield were observed. At 650° C. the methanol conversion was 81% and the formaldehyde yield was 71%.

EXAMPLE 3

A mixture of $CH_3OH$ and $N_2O$, in which the mole ratio of $CH_3OH$ to $N_2O$ was 1.82, was oxidized over a 0.5 g. bed of metallic silver at a contact time of 0.05 second. When the catalyst bed was maintained at 550° C., an 89% methanol conversion and a 62% formaldehyde yield were observed. At 600° C., the methanol conversion was 78% and the formaldehyde yield was 75%.

EXAMPLE 4

In a flow reactor, 0.5 g. of a catalyst containing 17% Ag supported on $\alpha$-$Al_2O_3$ (Harshaw Co.) was prereduced in situ in a stream of $H_2$/He at 300° C.

At temperatures of 600° C. and higher, $N_2O$ is quantitatively converted when feeds containing 20 to 40 mole percent $N_2O$ and 30 mole percent $CH_3OH$ are passed through the bed of catalyst. At 600° C., conversion of $CH_3OH$ is of the order of 75%, with the yield of HCHO in the range of 72–75%. At 625° C., conversion of $CH_3OH$ is 91% (after one hour on stream at that temperature) with the yield of HCHO being 52%. The contact time averaged 0.05 second.

When oxygen was substituted for $N_2O$ in the feed over the same catalyst, the conversion of methanol was lower than 50% and the formaldehyde yield was below 30% after two hours on stream at 600° C.

EXAMPLE 5

A copper-silver alloy containing 2.5 mole % of silver was prepared in the form of shavings about 2 mm. long. The alloy catalyst was oxidized during its preparation at high temperatures; its performance varied with aging in the reactor as a function of the extent of reduction in the feed mixture which contained 29.5 mole percent $CH_3OH$ and 38.5 mole percent $N_2O$.

Conversion of methanol was high on the fresh catalyst, while selectivity to formaldehyde was initially low. For example, there was an 87% $CH_3OH$ conversion at 600° C. (contact time averaged 0.05 second), and a 35% formaldehyde yield. After 3 hours on stream, conversion dropped to 58%, but the yield of formaldehyde rose to 72%. Further aging of the catalyst resulted in still lower conversions. At the same time, the unreacted $N_2O$ level in the off-gas increased with further aging of the catalyst, i.e., with increased reduction of the catalyst.

EXAMPLE 6

A silver-gold alloy catalyst in the form of shavings about 2 mm. in length and having an Ag:Au atomic ratio of 1:1 was used. After one hour on stream at 650° C. (contact time averaged 0.5 second), at 60% methanol conversion, a 60% formaldehyde yield was recorded using a feed containing 51 mole percent $CH_3OH$, 29.5 mole percent of $N_2O$ and the remainder helium. Increasing the concentration of $N_2O$ to 40 mole percent resulted in 98% conversion of methanol at 600° C., but decreased the formaldehyde yield to about 30%.

EXAMPLE 7

The following procedure was used to compare the use of air and nitrous oxide as an oxygen source. A 10 mm I.D. quartz tube was filled to a depth of 19.05 mm (¾ inch) with metallic silver catalyst which was in the form of irregular or polysurface granules in the 8–60 mesh particle size range. The catalyst section was heated externally to initiate the reaction, and once initiated, external heat was adjusted to run the process at the desired temperature. The bed and wall temperatures were recorded using appropriate thermocouples.

For evaluation of the oxygen source, liquid methanol (0.5 g/min.) was vaporized, mixed with enough preheated air or nitrous oxide to furnish the desired methanol conversion, and passed through the catalyst bed at 550°–650° C. The product was quickly cooled to below 200° C. and analyzed by gas chromatography to determine yield and conversion. The following results were obtained:

| MeOH Conversion % | Oxygen Source | Temp. °C. | Yield to HCHO % |
| --- | --- | --- | --- |
| 65.0 | $N_2O$ | 628 | 94.5 |
| 65.0 | Air | 620 | 92.5 |

EXAMPLE 8

The following comparative example illustrates a two-stage operation using air as the oxygen source in the first stage and nitrous oxide or air as the oxygen source in the second stage. Two-stage operation was carried out using two 10 mm I.D. quartz tubes filled with metallic silver catalyst as described in Example 7 in series. The procedure was similar to that used in Example 7 except that the product from the first stage was mixed with additional preheated air or nitrous oxide to furnish the desired overall methanol conversions. The conditions in the first stage were as follows:

MeOH conv.=65.0%
Yield to HCHO=92.5%
Temp.=620° C.
The following results were obtained in the second stage.

| Overall MeOH Conversion % | Oxygen Source in Second Stage | Second Stage Temp. °C. | Yield to HCHO % |
| --- | --- | --- | --- |
| 99.3 | $N_2O$ | 645 | 86.1 |
| 97.4 | $N_2O$ | 625 | 87.5 |
| 97.4 | Air | 615 | 82.2 |

EXAMPLE 9

The following comparative example illustrates the yield improvement obtained using either air or nitrous oxide as the oxygen source in both stages. Two-stage operation was carried out using the reactors described in Example 8. The following results were obtained.

| MeOH Conversion % | First Stage Temp. °C. | Oxygen Source | Sec. Stage Temp. °C. | Yield to HCHO % |
| --- | --- | --- | --- | --- |
| 95.2 | 590 | $N_2O$ | 570 | 89.2 |
| 96.8 | 590 | " | 600 | 89.5 |
| 98.7 | 590 | " | 640 | 88.5 |
| 92.6 | 565 | Air | 540 | 85.8 |
| 93.9 | 570 | " | 560 | 84.2 |
| 97.1 | 620 | " | 590 | 81.8 |
| 97.4 | 610 | " | 615 | 82.2 |

EXAMPLE 10

This example illustrates a supported catalyst containing a relatively low concentration of silver.

A 0.5 g. (0.446 cc)-portion of 10–20 mesh catalyst containing 3.5–4% Ag on $Al_2O_3$ was loaded into a quartz reactor surrounded by a furnace. A mixture of $CH_3OH$ (31.7 mole %) and $N_2O$ (20.1 mole %), i.e., $CH_3OH/N_2O = 1.58$, in helium was fed into the catalyst bed for a contact time of 0.035–0.030 seconds. After 10 minutes on stream at 630° C. the conversion of methanol was 83.6% and the yield of HCHO was 21.5%. After 93 minutes on stream, the conversion was 60% and the yield of HCHO was 67.6%.

INDUSTRIAL APPLICABILITY

The process described herein is suitable for commercial production of formaldehyde.

We claim:

1. The process of making formaldehyde which comprises continuously passing, for a contact time of 0.001 to 0.2 second, a gaseous mixture of methanol and nitrous oxide in a methanol to nitrous oxide mole ratio of 0.5 to 4.0, over a metallic silver, metallic silver: gold alloy, or metallic silver: copper alloy catalyst bed which is either unsupported or supported and contains at least about 3 weight percent silver metal, wherein the silver alloy present contains at least 2.5 mole percent silver maintained at a temperature of 475° to 675° C.

2. The process of claim 1 wherein the mole ratio of methanol to nitrous oxide is within the range of 1.0 to 2.5.

3. The process of claim 1 wherein the gaseous mixture of methanol and nitrous oxide is diluted with an inert gas.

4. The process of claim 3 wherein the gaseous mixture of methanol and nitrous oxide is diluted with helium.

5. The process of claim 1 wherein the catalyst is metallic silver.

6. The process of claim 1 wherein the catalyst is supported on an inert material.

7. The process of claim 6 wherein the catalyst is supported on alumina.

8. The process of claim 1 wherein the catalyst is a silver:gold alloy.

9. The process of claim 1 wherein the catalyst is a silver:copper alloy.

10. The process of claim 1 wherein the contact time is 0.001 to 0.1 second.

11. The process of claim 1 wherein the catalyst bed is maintained at a temperature of 550° to 650° C.

12. The process of claim 1 which comprises continuously passing, for a contact time of 0.001 to 0.005 seconds, a gaseous mixture of methanol and nitrous oxide, diluted with an inert gas, in a methanol to nitrous oxide mole ratio of 1.0 to 2.5, over a pure metallic silver catalyst bed maintained at a temperature of 550° to 650° C.

* * * * *